United States Patent [19]

van der Jagt

[11] Patent Number: Plant 6,466

[45] Date of Patent: Dec. 13, 1988

[54] CHRYSANTHEMUM NAMED "WHITE REMEMBER"

[75] Inventor: Martinus van der Jagt, Ter Aar, Netherlands

[73] Assignee: Chrysanthemum Breeders Association, N.V., Curacao, Netherlands Antilles

[21] Appl. No.: 3,542

[22] Filed: Jan. 15, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

A new and distinct cultivar of Chrysanthemum plant named White Remember, bearing medium sized white blossoms with a green or yellow center and a performance of fourteen days.

3 Drawing Sheets

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of Chrysanthemum plant which is a mutant of Chrysanthemum named Remember. The new cultivar was discovered by Martinus van der Jagt at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and white color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage of the new cultivar.

DESCRIPTION OF THE NEW PLANT

This new variety of Chrysanthemum is of the botanical classification *Chrysanthemum morifolium,* named White Remember. When grown in the vicinity of Ter Aar, Holland, it has a response time of approximately eight and a half weeks. This new variety produces medium sized white blooms with a green or yellow center having a performance of fourteen days. This new variety of Chrysanthemum has been found to retain its distinctive characteristics throughout successive propagations and may be planted under conventional greenhouse conditions in Holland between weeks 1 and 32.

The following is a description of the plant and characteristics that distinguish it over related known varieties and its antecedents:

Botanical classification: *Chrysanthemum morifolium.*

Bud:

*Size.*—Small (cross section: 0.8 cm, height: 1.0 cm).

*Form.*—Oval and high.

*Outside color.*—White 155C.

Bloom:

*Size.*—Medium.

*Fully expanded.*—7.5 cm.

*Borne.*—Single and several.

*Stems.*—Strong.

*Forms.*—Anemone type.

*Permanence.*—14 days (at 18°-20° C.).

Color:

*Center of flower (Disk Floret).*—The cushion 155B. The center spot of the cushion of a immature flower: 143C, mature flower: 11B.

*Base of petals.*—White 155D.

*Inside of petals.*—White 155D.

*Reverse of petals.*—White 155D.

*Outer petals.*—White 155D.

*Tonality from a distance.*—A white anemone type with a green or yellow spot depending on flowering stage of the flower.

*Discoloration.*—None.

Petals:

*Texture.*—Upperside: Smooth. Underside: Smooth.

*Number.*—23-26.

*Cross-section.*—Straight, two keels.

*Arrangement.*—Imbricated, two rows.

*Persistence.*—Normal. Petals reflex when overbloomed (after 14 days).

*Fragrance.*—Chrysanthemum.

Reproductive organs:

*Stamens.*—Some in the petals of the cushion.

*Pollen.*—None to some appears when blooming.

*Styles.*—Green/yellow (columnar); length (short): 3 mm.

*Stigmas.*—Green/yellow, 0.6 mm wide.

*Ovaries.*—Enclosed in calyx.

Plant:

*Form.*—Spray mum meant for erect culture.

*Growth.*—Medium to vigorous.

*Height.*—95-105 cm.

*Peduncle.*—Near the top: 13 cm. Near the Middle: 18 cm. Near the bottom: 26 cm.

*Internodes.*—3.5-4.5 cm.

*Flowering response.*—8½ weeks.

Foliage:

*Color.*—Upperside: Green 139A. Underside: Greyed green 189A.

*Size.*—Length: 10.5 cm. Width: 8 cm.

*Quantity.*—Average 26.

*Shape.*—Oval, deeply undulated, length: 10.5 cm, width: 8 cm.

*Texture.*—Upperside: Rough. Underside: Rough, very hirsute.

*Ribs and veins.*—Ribs and veins normally developed. Upperside: Ribs clearly defined; veins not. Underside: Ribs and veins clearly defined.

*Edge.*—Somewhat crenated.

In the description above, color references are made to the "R.H.S. Colour Chart" issued by The Royal Horticultural Society, in association with the Flower Council of Holland, Edition February 1986.

What is claimed:

1. A new and distinct cultivar of Chrysanthemum named White Remember, as described and illustrated in the foregoing specification and accompanying drawings.

* * * * *

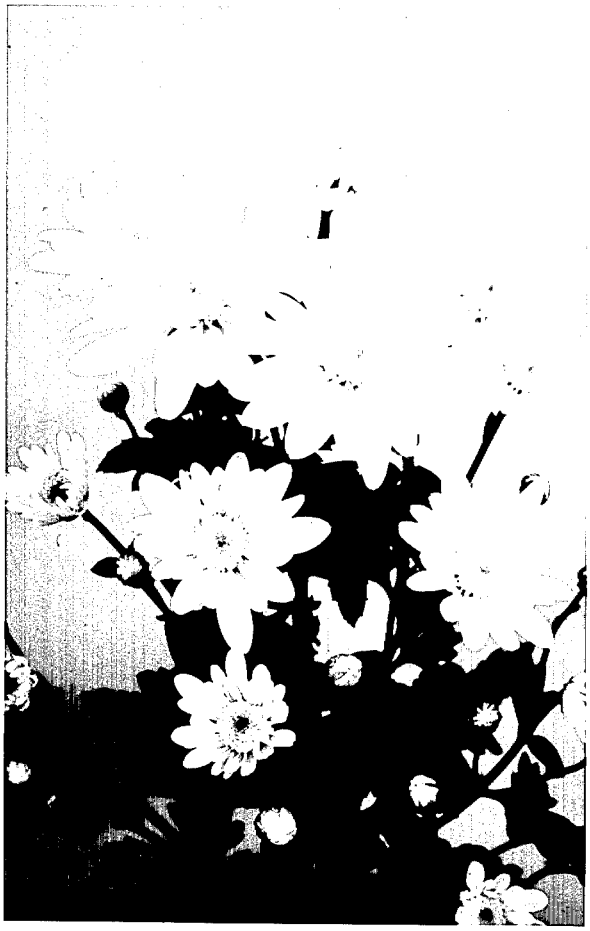

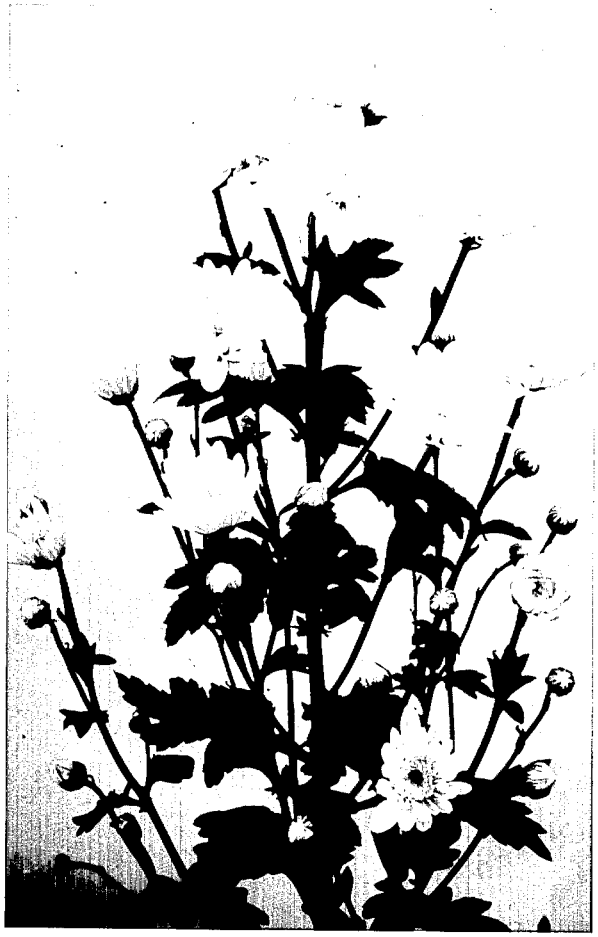

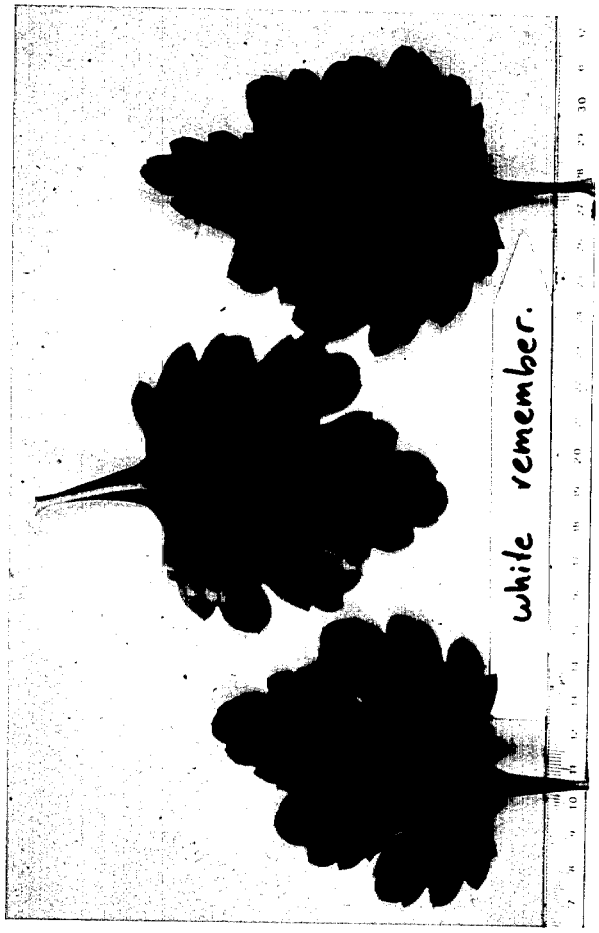
white remember.